United States Patent [19]

Baumgartner

[11] Patent Number: 5,171,280
[45] Date of Patent: Dec. 15, 1992

[54] INTERVERTEBRAL PROSTHESIS
[75] Inventor: Walter Baumgartner, Wil, Switzerland
[73] Assignee: Sulzer Brothers Limited, Winterthur, Switzerland
[21] Appl. No.: 673,276
[22] Filed: Mar. 21, 1991
[30] Foreign Application Priority Data Apr. 20, 1990 [CH] Switzerland .................... 01324/90

[51] Int. Cl.$^5$ .......................... A61F 2/44; A61F 2/30
[52] U.S. Cl. ........................................ 623/17; 623/18
[58] Field of Search ............... 623/17; 128/842, 843; 600/29, 30

[56] References Cited
U.S. PATENT DOCUMENTS

| | | | |
|---|---|---|---|
| 3,867,728 | 2/1975 | Stubstad et al. | 623/17 |
| 3,875,595 | 4/1975 | Froning | 3/1 |
| 3,883,902 | 5/1975 | Lynch | 3/36 |
| 4,932,969 | 6/1990 | Frey | 62/17 |

FOREIGN PATENT DOCUMENTS

| | | |
|---|---|---|
| 0176728 | 4/1986 | European Pat. Off. . |
| 0260080 | 3/1988 | European Pat. Off. . |
| 0277282 | 8/1988 | European Pat. Off. . |

Primary Examiner—David Isabella
Assistant Examiner—Dinh X. Nguyen
Attorney, Agent, or Firm—Kenyon & Kenyon

[57] ABSTRACT

The prosthesis has a valve at one end formed of a fixed base and a coiler body which is able to rotate on the base. A flexible elastic body defining a hollow chamber extends from the coiler body and is able to receive filling medium via the valve. A compact strand extends from the free end of the elastic body. An instrument is provided for implanting the prosthesis between two vertebrae along with a drive belt for rotating the coiler body about the fixed base and, thus the elastic body about the coiler body. Filling of the elastic body takes place after coiling.

20 Claims, 4 Drawing Sheets

INTERVERTEBRAL PROSTHESIS

This invention relates to an intervertebral prosthesis.

As is known, various types of prostheses have been known for implanting between two vertebrae. For example, U.S. Pat. No. 3,875,595 describes an intervertebral disc prosthesis of collapsible bladder-like construction which can be inserted between two vertebrae adjacent to an injured disc and thereafter expanded from a flattened condition. To this end, fluid is pumped through a check valve in the prosthesis in order to expand the prosthesis so that the prosthesis may then function as a nucleus of a natural disc. With this construction, a damaged cartilaginous disc core (nucleus pulposus) is to be replaced by a bubble-like cushion of elastic material which may be filled with an incompressible medium. In addition, the outer rim (annulus fibrosus) of a natural cartilaginous disc is to be largely preserved.

U.S. Pat. No. 3,875,595 also describes a tubular instrument which is provided through which the inflatable prosthesis is to be implanted in a collapsed state, anchored in the adjacent vertebrae and subsequently filled. In the case of this construction, the annulus fibrosus must completely absorb, as radial forces, the compressive forces generated in the case of loading in the nucleus.

European Patent No. Application 0277282 describes an intervertebral prosthesis which is formed of a hollow cushion filled with an incompressible medium. In addition, on a surface exposed to a vertebrae, the prosthesis is provided with a structure into which bone tissue may grow for locating purposes. In this construction, the whole cartilaginous disc is to be replaced. To this end, a relatively wide opening must be left free ventrally between the vertebrae since this prosthesis is implanted in the already filled state.

European Patent Application 0176728 describes an intervertebral prosthesis which is defined by a sliding body disposed on a fixed center of rotation which, as has been proved, does not correspond with the facts in the processes of movement in a spinal column. To do that, the cover plates become loaded to a greater extent, which may lead to a sinking in of the implant.

Accordingly, it is an object of the invention to create an implant as a replacement for the nucleus of a cartilaginous disc.

It is another object of the invention to provide an intervertebral prosthesis which can be readily implanted in place between two vertebrae.

It is another object of the invention to provide an intervertebral prosthesis of relatively simple construction.

It is another object of the invention to provide an intervertebral prosthesis which can be easily implanted.

Briefly, the invention provides an intervertebral prothesis having an elastic liquid-tight hollow body defining an elongated chamber for receiving an incompressible free-flowing medium and a valve connected to the body at one end for supplying an incompressible free-flowing medium into the chamber while being disposed for coiling of the body thereon. The prosthesis may also have a compact strip extending from an opposite end of the body.

The construction of the prosthesis is such that the valve may be turned about an axis so that the elastic body can be coiled about the valve.

The prosthesis, once implanted, is able to absorb the radial forces which are exerted upon the periphery via the incompressible medium in the chamber. In addition, the prosthesis requires only a relatively slight operation in the intervertebral region through an opening as small as possible.

The valve of the prosthesis is constructed with a fixed base having a first tubular portion for conveying a free-flowing medium and a coiler body which is rotatably mounted on the base and secured to the elastic body in order to permit coiling of the elastic body thereon. In addition, the coiler body has a second tubular portion in communication with the tubular portion of the base as well as the chamber in order to deliver a free-flowing medium to the chamber of the elastic body.

The invention further provides an instrument for implanting the intervertebral prosthesis. In this regard, the instrument is formed of a tubular guidepiece having a pair of axial channels one of which is to convey the free-flowing medium to the chamber of the elastic body while the other chamber is sized to receive a drive means for rotating the coiler body of the prosthesis about a central axis in order to effect coiling of the elastic body about the valve. The instrument is also provided with means at one end for detachable connection to the valve.

During implantation, with the valve to the front, the prosthesis is introduced into a space which was occupied by a previously removed nucleus pulposus. The coiler body is then rotated so that the elastic body is coiled about the coiler body before the chamber of the elastic body is filled. Thus, in a similar manner as described in U.S. Pat. No. 3,875,595, the prosthesis can be implanted dorsally through a simple tube. After coiling of the elastic body, a free-flowing medium can be introduced through the second passage of the instrument so that the elastic body is expanded to the extent desired.

After the coiled elastic body has been filled with medium, the drive means which has been fitted through the instrument can be disconnected and the instrument removed, leaving the prosthesis in place.

During coiling, the compact strip at the opposite end of the elastic body is also coiled about the valve. This compact strip serves to provide the required capability of absorbing radial forces. In addition, after coiling, the compact strip can be fixed at the end to the previous winding.

The prosthesis does not exhibit any fixed center of rotation Furthermore, any cover plates which are provided during the overall operation are loaded as in case of the natural nucleus pulposus. Finally, the function of the annulus fibrosus is reinforced by the prosthesis.

The chamber and the strip advantageously consist of one piece and of a textile structure—i.e., for example, a fabric, a weave, knitting or a braid—which is partially enveloped by an elastomer in order to avoid abrasion of the textile structure. Moreover, it has proved advantageous, if the height of the chamber running in parallel with the axis of rotation of the valve is greater than its width, in which case the cross-section may, for example, be at least approximately rectangular. Through these two measures, a coiled body results, the turns of which rest against one another by relatively large smooth areas of contact, a number of turns being formed in coiling up, which in turn facilitate adaptation to the shape of the cavity into which the prosthesis is being inserted. This adaptation may be still further assisted if the height of the chamber is variable.

It is advantageous if the means for connection of the instrument to the valve consists of pins which engage in the fixed base of the valve by projecting from the end face of the guidepiece. Moreover, the drive means for rotation of the coiler body is advantageously an endless belt with a ribbed surface, the ribbing on which engages in a toothed ring on the coiler body.

These and other objects and advantages of the invention will become more apparent from the following detailed description taken in conjunction with the accompanying drawings wherein:

FIG. 1 diagrammatically illustrates a cross-sectional view of an intervertebral prosthesis constructed in accordance with the invention;

Figure 1:
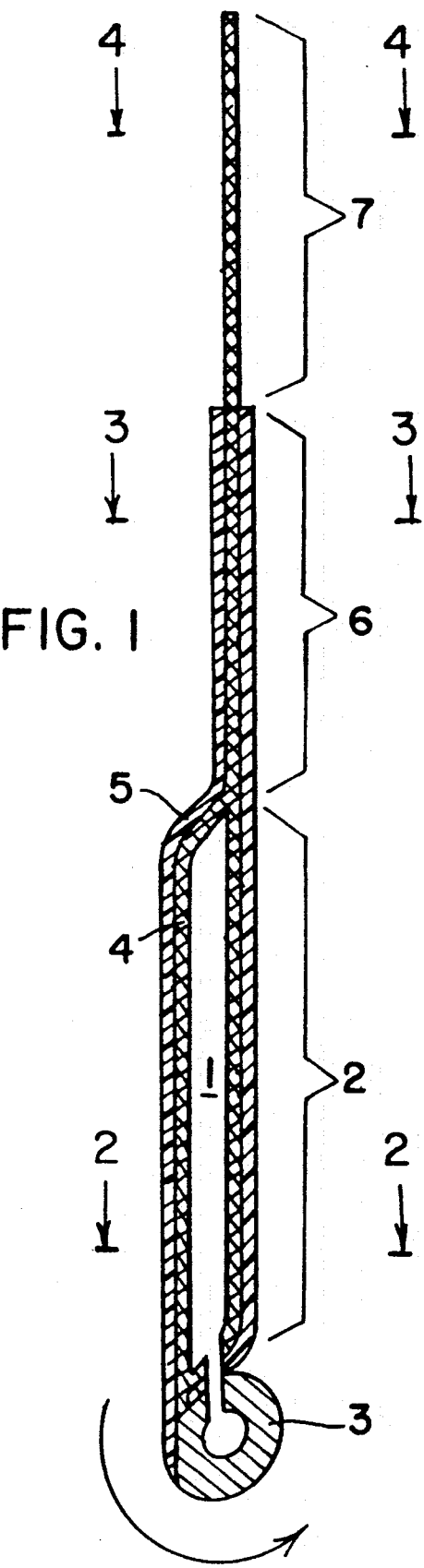

Referring to FIG. 1, the intervertebral prosthesis is constructed of an elastic liquid-tight hollow body 2 which defines an elongated chamber 1 for receiving an incompressible free-flowing medium. In addition, the hollow body 2 is connected to a valve 3 at one end thereof. This valve 3 serves to supply an incompressible free-flowing medium into the chamber 1 as well as for coiling of the body 2 thereon as described below.

Figure 2:
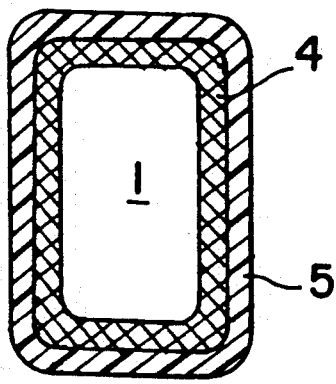
FIG. 2 illustrates a cross-sectional view taken on line II—II of FIG. 1.

Referring to FIG. 2, the elastic and flexible hollow body 2 consists of a meshwork 4 manufactured from plastic threads, for example, polyethylene terephthalate, which by means of a dip method is coated on the outside with a layer of elastomer 5, for example, a polyurethane. The polyurethane layer has the duty of preventing rubbing of the textile threads against one another with the implant inserted.

Figure 4:
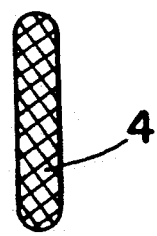
FIG. 4 illustrates a cross-sectional view taken on line IV—IV of FIG. 1.
Figure 3:
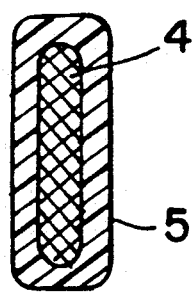
FIG. 3 illustrates a cross-sectional view taken on line III—III of FIG. 1.
Figure 7:
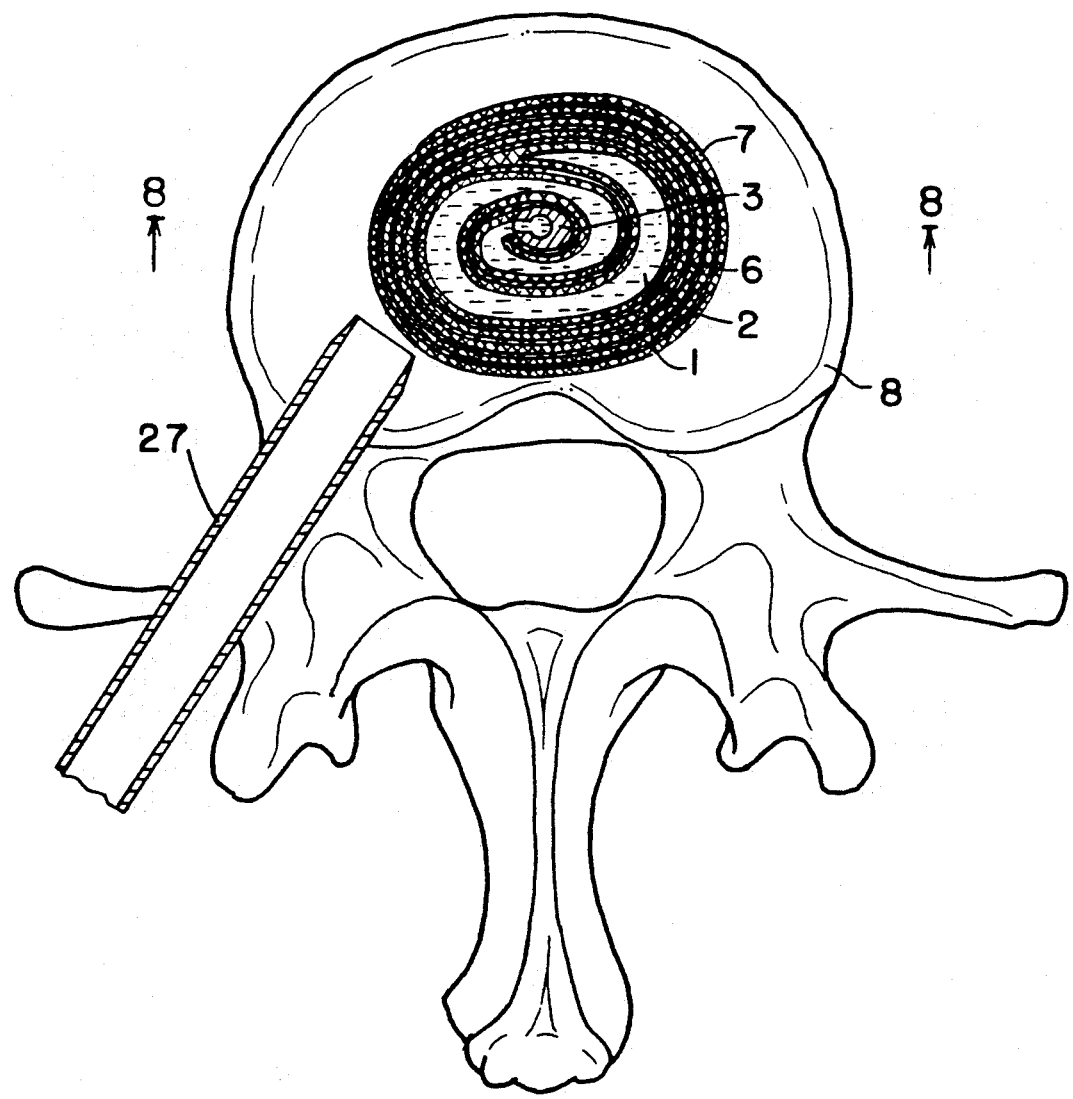
FIG. 7 illustrates a view of a vertebrae from above with the prosthesis in an implanted coiled state in accordance with the invention.

As shown in FIG. 1, the body 2 of the prosthesis continues into a compact textile strip 6 which is likewise coated over a certain length with further elastomer 5 (see FIG. 3), but which at a free end 7 (FIG. 4) no longer carries any coating 5. Hence, in the case of a prosthesis implanted between two vertebrae 8 (FIGS. 7 and 8), the free end 7 may be fixed relatively simply onto itself by stitching or welding.

Figure 6:
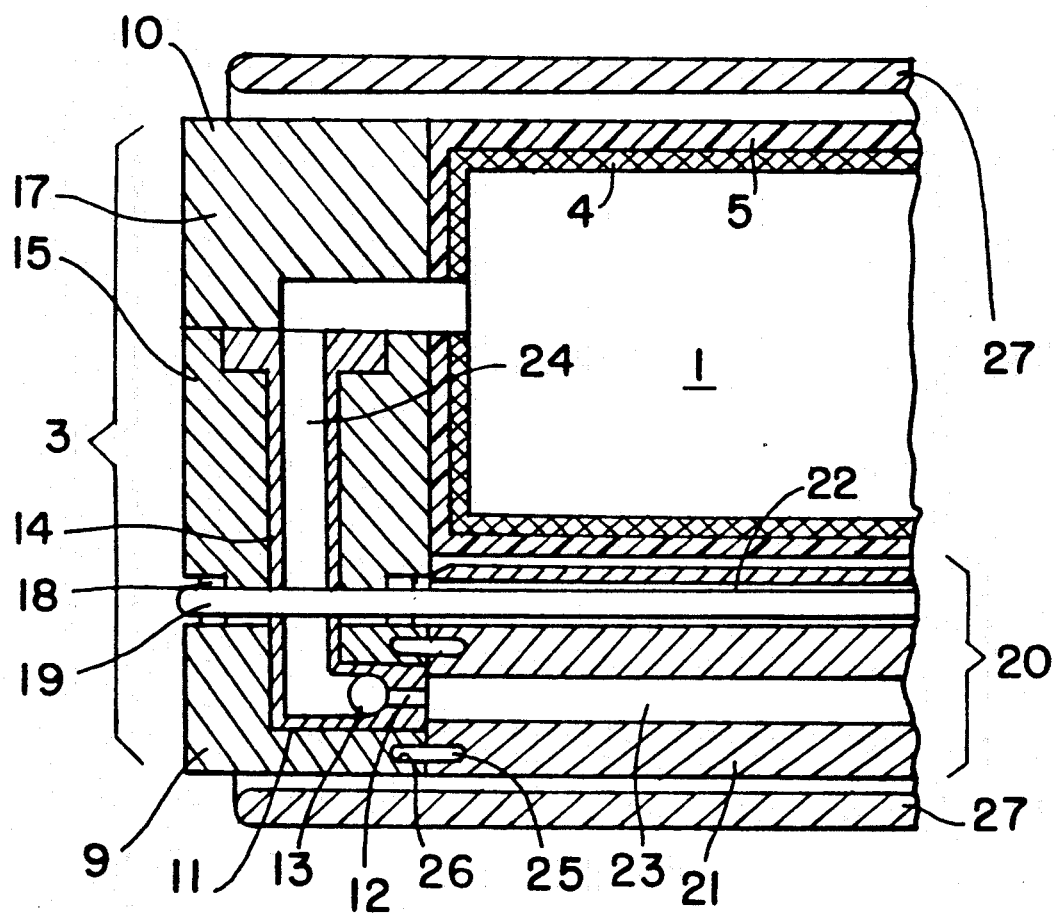
FIG. 6 illustrates a view of the prosthesis of FIG. 1 mounted on the instrument of FIG. 5 in accordance with invention.

Referring to FIG. 6, the valve 3 is composed of a fixed base 9 and a turnable coiler body 10. Both the base 9 and body 10 consist, for example, of a compatible metal such as titanium or a titanium alloy. The fixed base 9 contains a first tubular portion 11 consisting, for example, of stainless example, a metal ball 13 as a check valve.

A second tubular portion 14 is connected to the tubular portion 11 and leads into the chamber 1 of the hollow body 2. This portion 14 serves, at the same time, as a fixed pivot for the turnable coiler body 10. For reasons of assembly, the coiler body 10 is subdivided into a lower part 15 which surrounds the tubular portion 14 and an upper part 17. At the bottom, the lower part 15 is made as a toothed ring 18 in which a drive means in the form of an endless driving belt 19 engages, which consists, for example, of a plastics reinforced with glass fiber.

Figure 5:
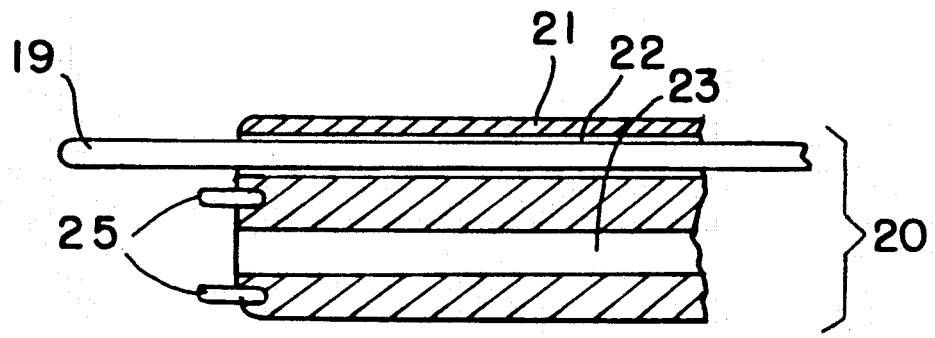
FIG. 5 illustrates a cross-sectional view of an instrument used for implanting the prosthesis in accordance with the invention.

The driving belt 19 is part of an instrument 20 shown in FIG. 5, for the introduction, coiling up and filling of the prosthesis. In the present example, the instrument 20 consists essentially of a metal guidepiece 21 in which two parallel longitudinal bores or channels 22 and 23 are provided. One bore 22 receives the driving belt 19, whilst the other bore 23 which may be connected to the tubular portion 11 of the valve base 9 is provided for feeding the incompressible filling medium, for example, hydroxin ethyl methacrylate into the chamber 1. In that case, the filling medium flows in through the non-return check valve consisting of the valve-seat 12 and closure 13 via a path of flow 24 in the tubular portions 11 and 14 and the upper part 17 of the chamber 1.

For a rigid but detachable connection of the guidepiece 21 to the valve base 9, means in the form of two pins 25 are provided in the end face of the guidepiece 21, which may be inserted in corresponding recesses 26 of the valve part 9.

For implantation, the prosthesis together with this guiding instrument 20 is accommodated in a tube 27, as indicated in FIG. 6.

Figure 8:
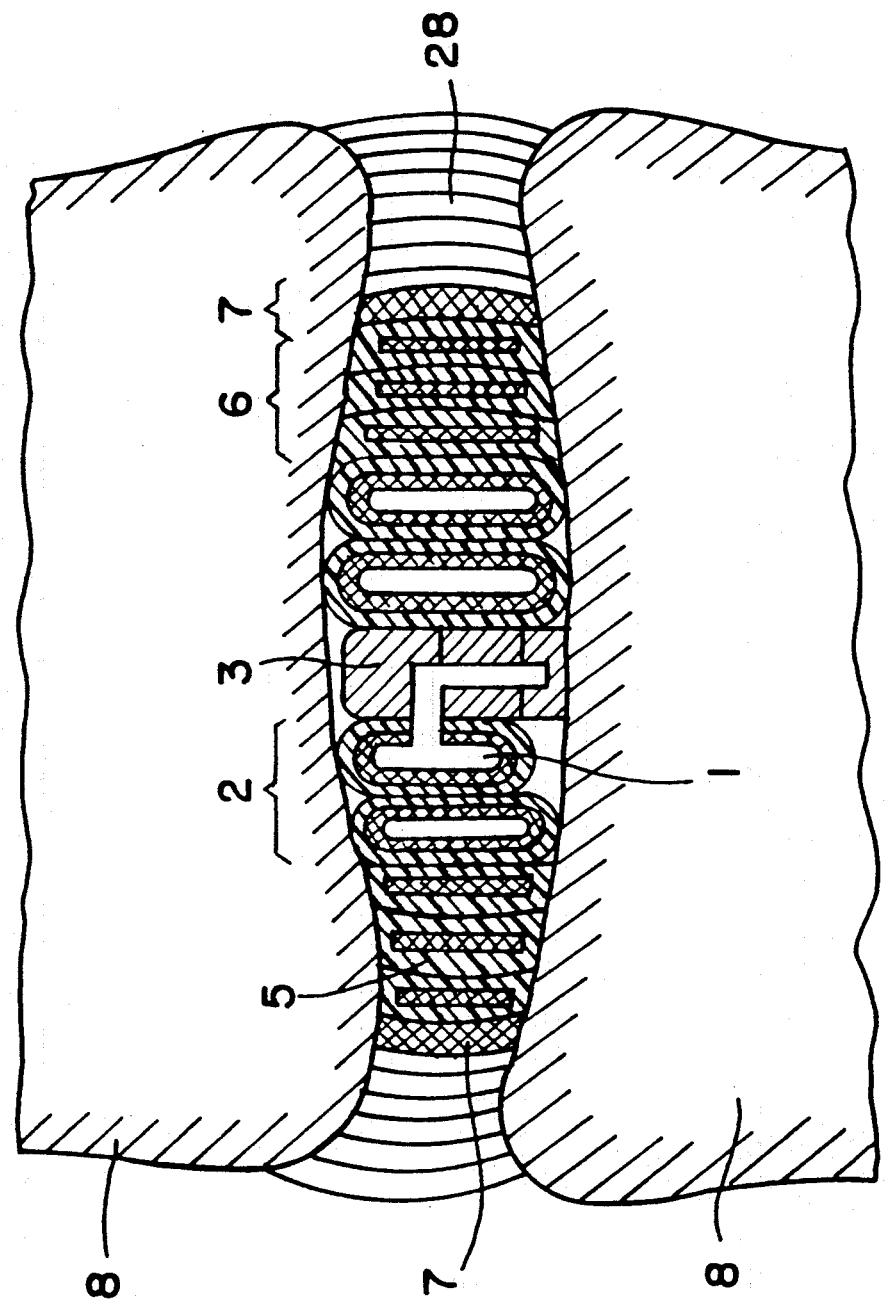
FIG. 8 illustrates a view taken on line VIII—VIII of FIG. 7.

In FIG. 8, the natural tissue of the annulus fibrosus which surrounds the implant 1 is designated by 28.

The insertion of the prosthesis between two vertebrae 8 may, for example, in a similar way to the implant according to the U.S. Pat. No. 3,875,595 mentioned initially, be effected dorsally through the tube 27. For introduction between the vertebrae, only a relatively slight operation is necessary. After "placing" of the tube 27, the nucleus pulposus and, if necessary, damaged parts of the annulus fibrosus are removed and subsequently the prosthesis which has been previously connected rigidly to the instrument 20 is introduced through the tube 27 into the cavity which has been left.

After the valve 3 has been brought into the required position, the striplike part 2, 6, 7 of the prosthesis is coiled on to the valve 3 by pulling on one side of the driving belt 19. After completion of the coiling process, the free end 7 of the prosthesis is fixed to itself by welding or stitching and the belt 19 is severed and removed. Now, the chamber 1 is filled with filling medium through the bore 23 in the guidepiece 21. When the desired amount of filling medium has been filled in, the guidepiece 21 is loosened from the valve base 9 and removed through the tube 27. Subsequently, the tube 27 is also removed from the body.

The prosthesis thus fulfills two requirements for the overall implant. First, the strip extending from the end of the prosthesis is able to surround the filled chamber externally in order to guarantee that the radial forces which arise upon loading are absorbed by the implant and do not load the natural tissue of the annulus fibrosus. Second, the filling of the chamber after insertion and coiling about the valve allows the prosthesis to be implanted through a relatively small operation which requires only a small opening.

What is claimed is:

1. An intervertebral prosthesis comprising
an elastic liquid-tight hollow body defining an elongated chamber for receiving an incompressible free-flowing medium, said body including opposing ends;

a valve connected to said body at one end thereof for supplying an incompressible free-flowing medium into said chamber and attached to means for enabling said body to coil about said valve; and a compact strip extending from an opposite end of said body.

2. A prosthesis as set forth in claim 1 wherein each of said body and said strip is made of a textile structure and which further comprises an elastomer coating on each of said body and said strip.

3. A prothesis as set forth in claim 1 wherein said chamber has a height and a cross-sectional width and wherein said height is greater than said cross-sectional width.

4. A prosthesis as set forth in claim 3 wherein said chamber has a rectangular cross-section.

5. A prosthesis as set forth in claim 4 wherein said chamber has a longitudinal length and wherein said chamber has a variable height along the longitudinal length.

6. A prosthesis as set forth in claim 5 wherein said valve includes a fixed base having a first tubular portion including a valve seat and a closure means for seating on said valve seat, and a rotatable coiler body mounted on said fixed base and having a second tubular portion communicating with said first tubular portion and said chamber of said body, said coiler body being secured to said hollow body.

7. A prosthesis as set forth in claim 6 wherein said coiler body has a toothed ring thereon for engagement with a driving belt to effect rotation of said coiler body on said fixed base and winding of said hollow body about said coiler body.

8. An intervertebral prosthesis comprising an elastic liquid-tight body defining an elongated chamber; and a valve in communication with said chamber to deliver a free-flowing medium thereto; said valve including a fixed base having a first tubular portion for conveying a free-flowing medium therethrough and a coiler body rotatably mounted on said base and secured to said elastic body to permit coiling of said elastic body thereon, said coiler body having a second tubular portion in communication with said first tubular portion and said chamber to deliver a free-flowing medium to said chamber.

9. A prosthesis as set forth in claim 8 wherein said coiler body has a toothed ring thereon for engagement with a driving belt to effect rotation of said coiler body on said fixed base and winding of said elastic body on said coiler body.

10. A prosthesis as set forth in claim 8 wherein said elastic body is made of a textile structure and which further comprises an elastomer coating on said elastic body.

11. A prosthesis as set forth in claim 8 wherein said chamber has a height and a cross-sectional width and wherein said height is greater than said cross-sectional width.

12. A prothesis as set forth in claim 11 wherein said chamber has a rectangular cross-section.

13. An instrument for implanting an intervertebral prosthesis comprising a tubular guidepiece with at least one end and having a pair of axial channels, one of said channels being sized to convey a free-flowing medium therethrough to a chamber of a prosthesis and the other of said chamber being sized to receive a drive means for rotating the prosthesis about a central axis thereof; and means at one end of said guidepiece for detachable connection to the prosthesis.

14. An instrument as set forth in claim 13 wherein said means at said one end includes a plurality of pins projecting from said end.

15. An instrument as set forth in claim 13 wherein said drive means is an endless belt having a ribbed surface for engaging a toothed ring on the prosthesis.

16. In combination a prosthesis including an elastic body having an internal chamber and a valve secured to said body at one end thereof, said valve including a fixed base having a first tubular portion for conveying a free-flowing medium therethrough and a rotatable coiler body mounted on said base and secured to said elastic body to permit coiling of said elastic body thereon, said coiler body having a second tubular portion in communication with said first tubular portion and said chamber to deliver a free-flowing medium to said chamber;

an instrument for inserting said prosthesis between two vertebrae, said instrument including a tubular guidepiece having a pair of channels, one of said channels being in communication with said chamber to convey a free-flowing medium to said chamber; and drive means passing through the other of said channels for rotating said coiler body relative to said base to coil said elastic body about said coiler body.

17. The combination as set forth in claim 16 wherein said coiler body has a toothed ring thereon and said drive means is an endless belt having a ribbed surface engaging said ring.

18. The combination as set forth in claim 16 wherein said instrument has means at one end for engaging with said valve base.

19. The combination as set forth in claim 18 wherein said means at said one end includes a plurality of pins projecting from said end.

20. The combination as set forth in claim 16 wherein said valve base has a check valve in said one passage.

* * * * *

UNITED STATES PATENT AND TRADEMARK OFFICE
CERTIFICATE OF CORRECTION

PATENT NO. : 5,171,280

DATED : December 15, 1992

INVENTOR(S) : Baumgartner

It is certified that error appears in the above-indentified patent and that said Letters Patent is hereby corrected as shown below:

Column 2, line 21, change "chamber" to --channel--;

Column 3, line 26, after "with" insert --the--;
        line 61, after "stainless" insert --steel, into which are built a metal value-seat 12 and, for--;

Column 6, line 21, change "chamber" to --channels--.

Signed and Sealed this

Twenty-sixth Day of April, 1994

*Attest:*

BRUCE LEHMAN

*Attesting Officer*     *Commissioner of Patents and Trademarks*